US012611155B2

(12) United States Patent
Choi et al.

(10) Patent No.: US 12,611,155 B2
(45) Date of Patent: Apr. 28, 2026

(54) METHOD FOR PROVIDING INFORMATION NECESSARY FOR EVALUATING SEVERITY OF CORONARY ARTERY STENOSIS

(71) Applicants: JEJU NATIONAL UNIVERSITY INDUSTRY-ACADEMIC COOPERATION FOUNDATION, Jeju-si (KR); JEJU NATIONAL UNIVERSITY HOSPITAL, Jeju-si (KR)

(72) Inventors: Joon Hyouk Choi, Jeju-si (KR); Dong Guk Paeng, Jeju-si (KR); Gwan Suk Kang, Seogwipo-si (KR); Woong Bin Kang, Jeju-si (KR)

(73) Assignees: JEJU NATIONAL UNIVERSITY INDUSTRY-ACADEMIC COOPERATION FOUNDATION, Jeju-si (KR); JEJU NATIONAL UNIVERSITY HOSPITAL, Jeju-si (KR)

( * ) Notice: Subject to any disclaimer, the term of this patent is extended or adjusted under 35 U.S.C. 154(b) by 272 days.

(21) Appl. No.: 18/282,821

(22) PCT Filed: Mar. 21, 2022

(86) PCT No.: PCT/KR2022/003894
§ 371 (c)(1),
(2) Date: Sep. 19, 2023

(87) PCT Pub. No.: WO2022/197165
PCT Pub. Date: Sep. 22, 2022

(65) Prior Publication Data
US 2024/0164734 A1 May 23, 2024

(30) Foreign Application Priority Data
Mar. 19, 2021 (KR) ........................ 10-2021-0036100

(51) Int. Cl.
*A61B 6/50* (2024.01)
*A61B 5/026* (2006.01)
(Continued)

(52) U.S. Cl.
CPC .............. *A61B 6/504* (2013.01); *A61B 5/026* (2013.01); *A61B 6/481* (2013.01); *G06T 7/0012* (2013.01);
(Continued)

(58) Field of Classification Search
CPC ......... A61B 6/504; A61B 5/026; A61B 6/481; A61B 5/055; A61B 5/02007;
(Continued)

(56) References Cited

U.S. PATENT DOCUMENTS

2013/0132054 A1* 5/2013 Sharma .................. G16H 30/40
703/9
2014/0121513 A1* 5/2014 Tolkowsky ............... G06T 7/20
600/431
(Continued)

FOREIGN PATENT DOCUMENTS

JP       2013010005       1/2013
KR     20150058948       5/2015
(Continued)

OTHER PUBLICATIONS

Kang, Ung Bin et al., "Contrast intensity analysis for diagnosing stenosis in the coronary artery", The 11th National Congress on Fluid Engineering, Aug. 12, 2020, pp. 62-63.
(Continued)

*Primary Examiner* — Siamak Harandi
(74) *Attorney, Agent, or Firm* — LEX IP MEISTER, PLLC

(57) ABSTRACT
The present disclosure relates to a method for providing information necessary for assessing severity of coronary
(Continued)

artery stenosis, the method includes: administering a contrast agent to a coronary artery; capturing an angiographic image; setting a suspected stenosis area where stenosis is suspected and a proximal area where blood passes before the suspected stenosis area within region of captured image for observing the coronary artery stenosis based on the captured angiographic image; fixing position of the coronary artery where the contrast agent is administered by image processing; and deriving a blood flow velocity ratio, which is a relative ratio of blood flow in the proximal area and the suspected stenosis area, based on time when brightness changes in the proximal area and the suspected stenosis area of the captured image.

2 Claims, 7 Drawing Sheets

(51) Int. Cl.
> *A61B 6/00* (2006.01)
> *G06T 7/00* (2017.01)
> *G06V 10/25* (2022.01)

(52) U.S. Cl.
> CPC .... *G06V 10/25* (2022.01); *G06T 2207/30104* (2013.01)

(58) Field of Classification Search
> CPC ... A61B 5/02028; A61B 5/0275; A61B 5/352; A61B 5/7285; A61B 5/346; A61B 6/4417; A61B 6/5217; G06T 7/0012; G06T 2207/30104; G06V 10/25
> See application file for complete search history.

(56) References Cited

U.S. PATENT DOCUMENTS

| | | | | |
|---|---|---|---|---|
| 2014/0266577 A1* | 9/2014 | Anderson | ............ | A61B 5/6851 340/5.2 |
| 2014/0368526 A1* | 12/2014 | Day | ......................... | G06T 5/94 345/589 |
| 2016/0022236 A1* | 1/2016 | Ohishi | ................... | G16H 50/30 600/431 |

FOREIGN PATENT DOCUMENTS

| | | |
|---|---|---|
| KR | 102217392 | 2/2021 |
| KR | 20210027035 | 3/2021 |
| WO | 2020107667 | 6/2020 |

OTHER PUBLICATIONS

EPO, supplementary European search report of EP 22771831.9, dated Apr. 28, 2025, total 7 pages.

EPO, partial supplementary European search report of EP 22771831.9 dated Feb. 6, 2025, total 8 pages.

Kang Wongbin et al., "The evaluation for physiologic stenosis in the coronary artery using contrast intensity analysis", 64th Annual Scientific Meeting of the Korean Society of Cardiology, Oct. 16, 2020 (Oct. 16, 2020), XP093243151, Retrieved from the Internet: URL:https://www.ksc2020.or.kr/eng/program/session.php?scode=135, total 1 page.

EPO, Office Action of EP 22771831.9 dated Jan. 28, 2026, total 13 pages.

* cited by examiner

[Fig 1]
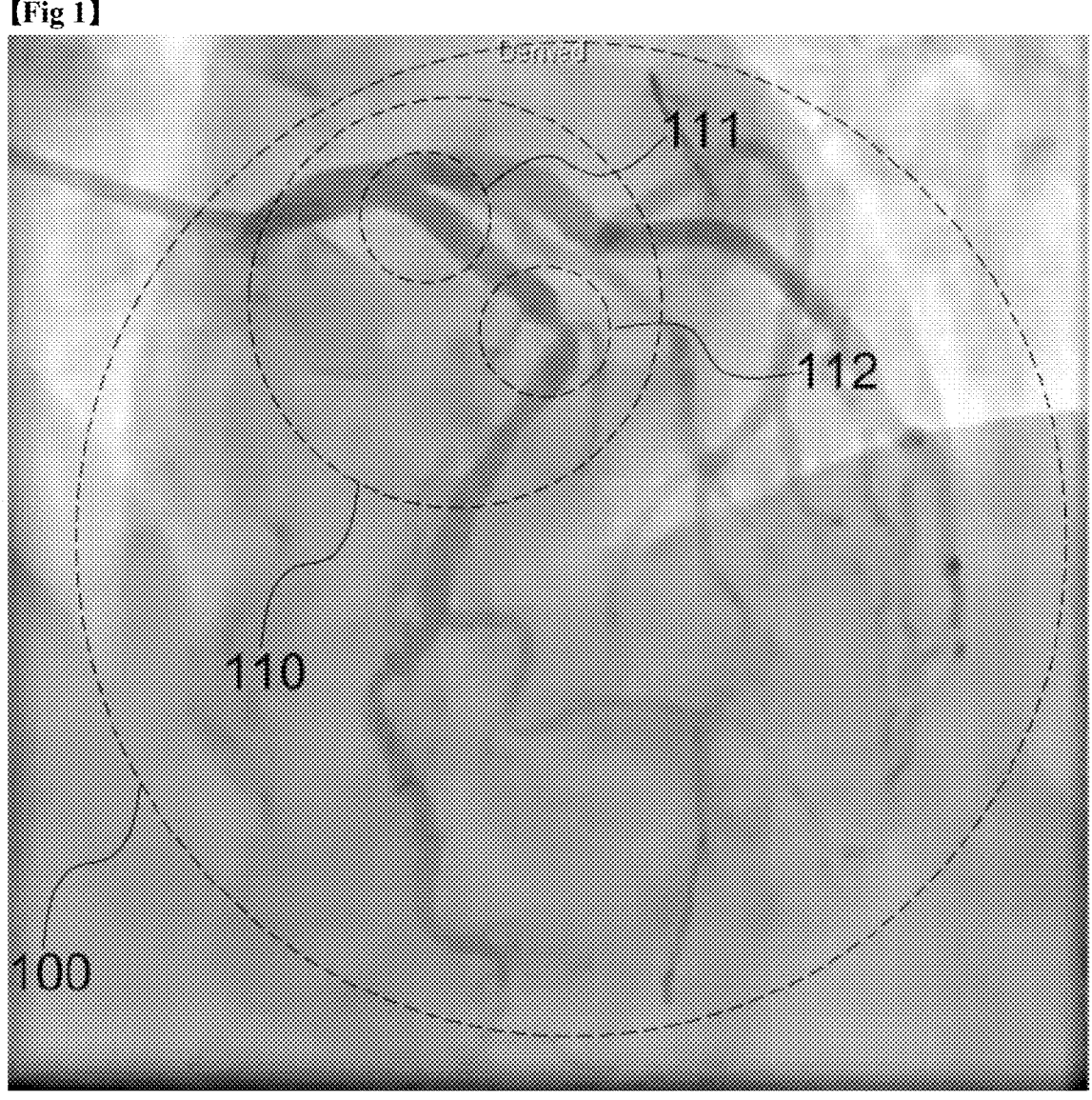

[Fig 2]
a                                    b
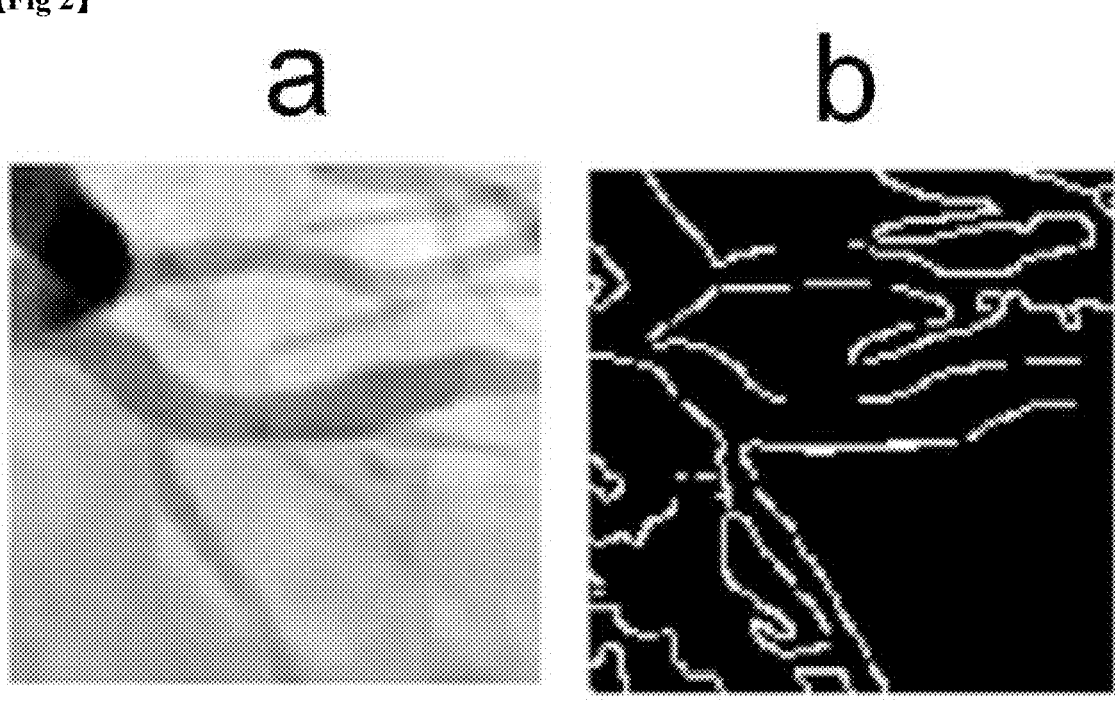

[Fig 3]
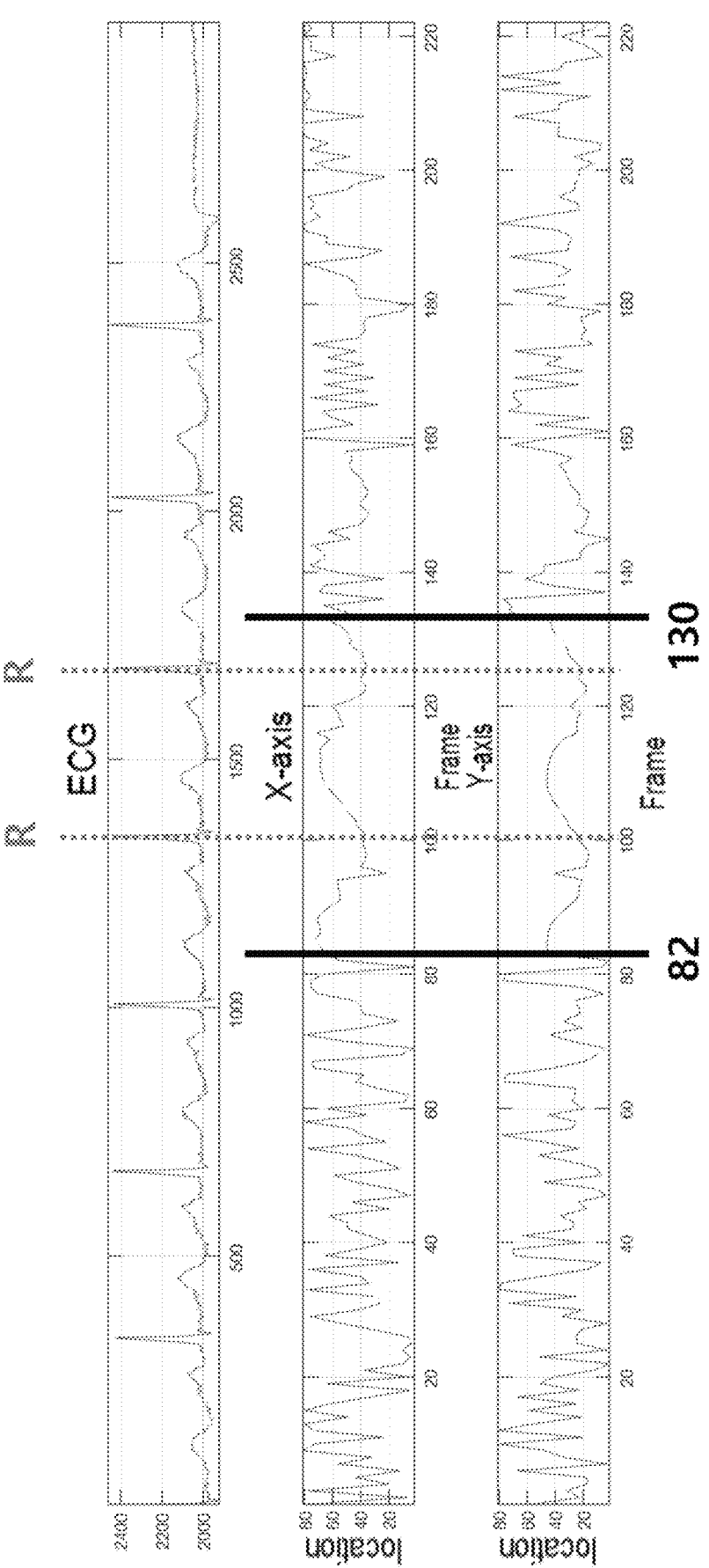

[Fig 4]
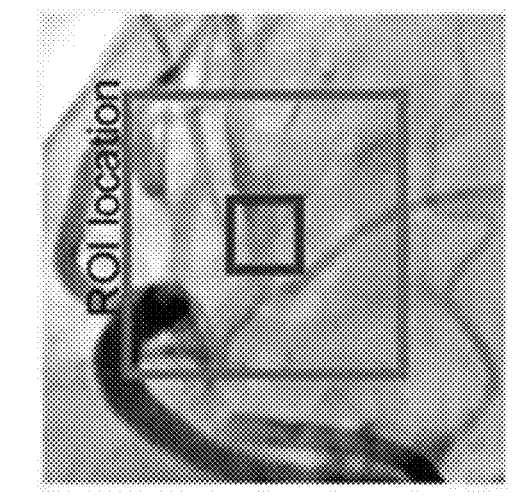
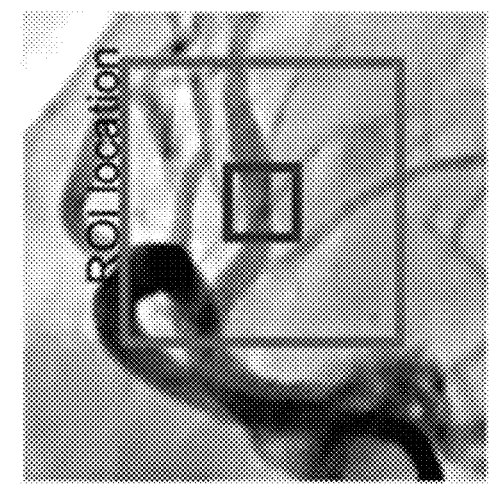
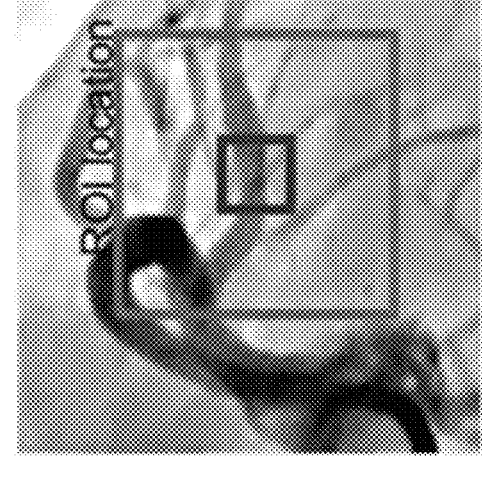
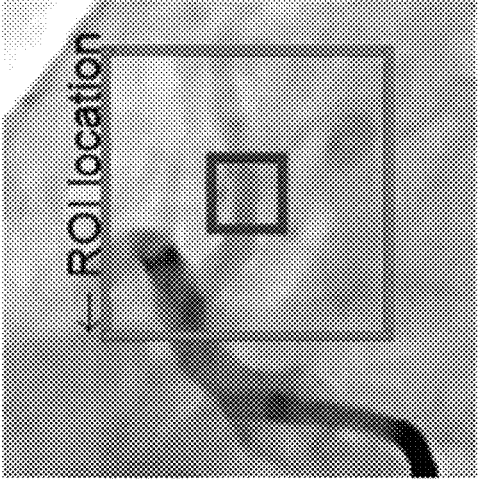

[Fig 5]
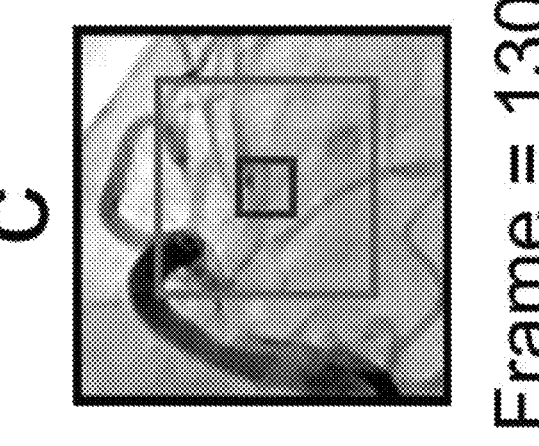
c
Frame = 130
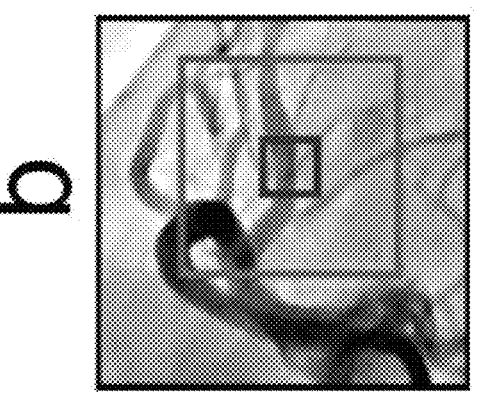
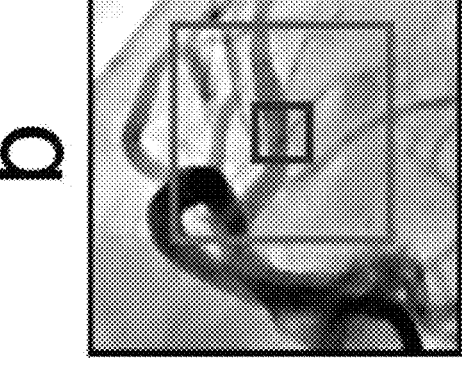
b
Frame = 107
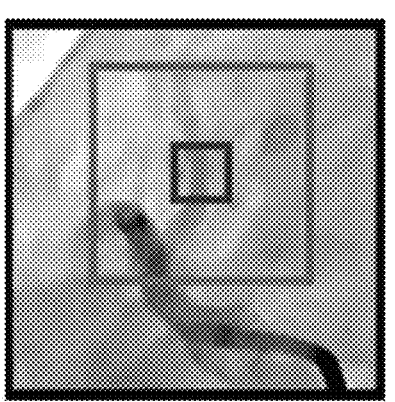
a
Frame = 82

[Fig 6]
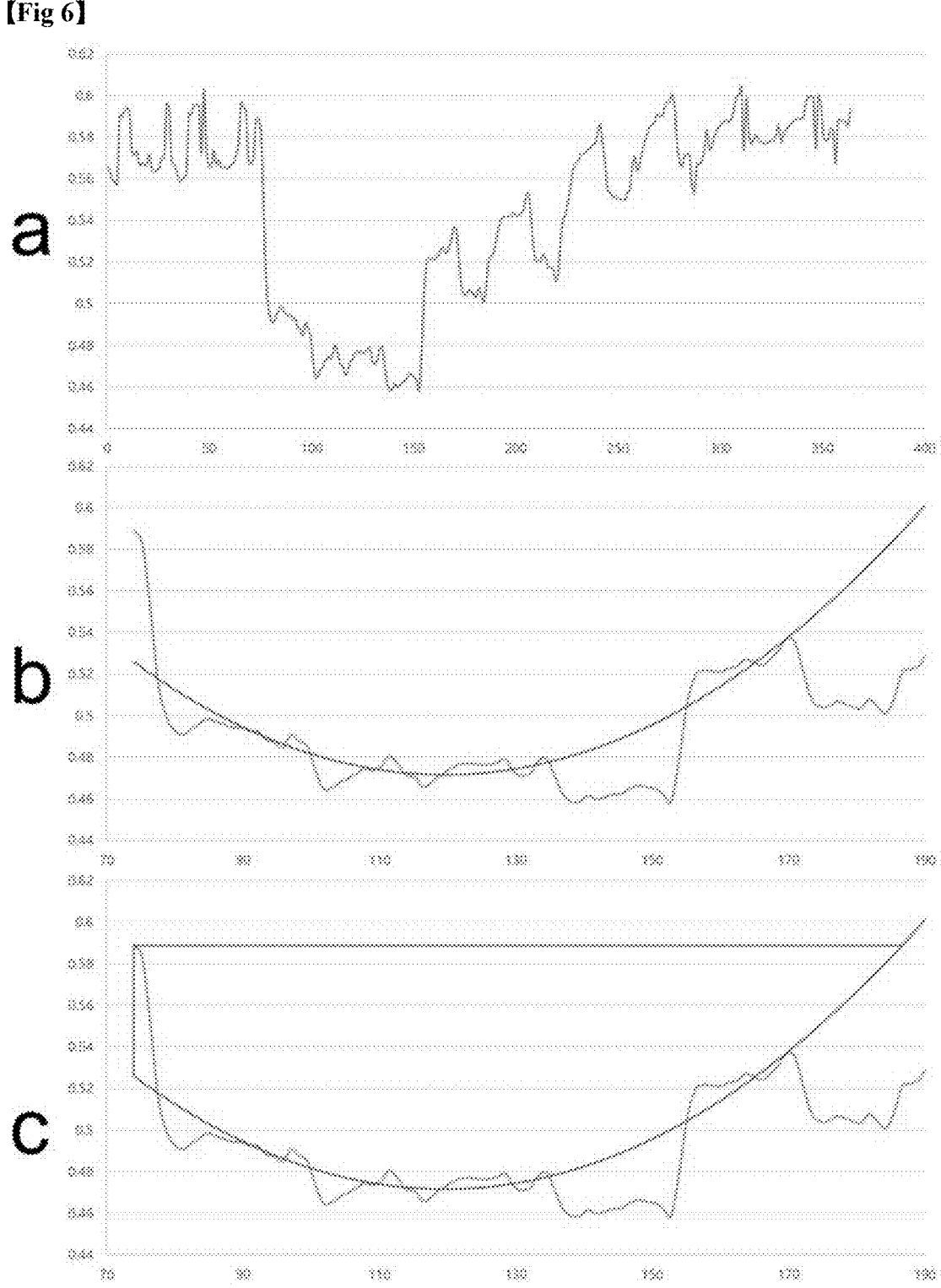

【Fig 7】
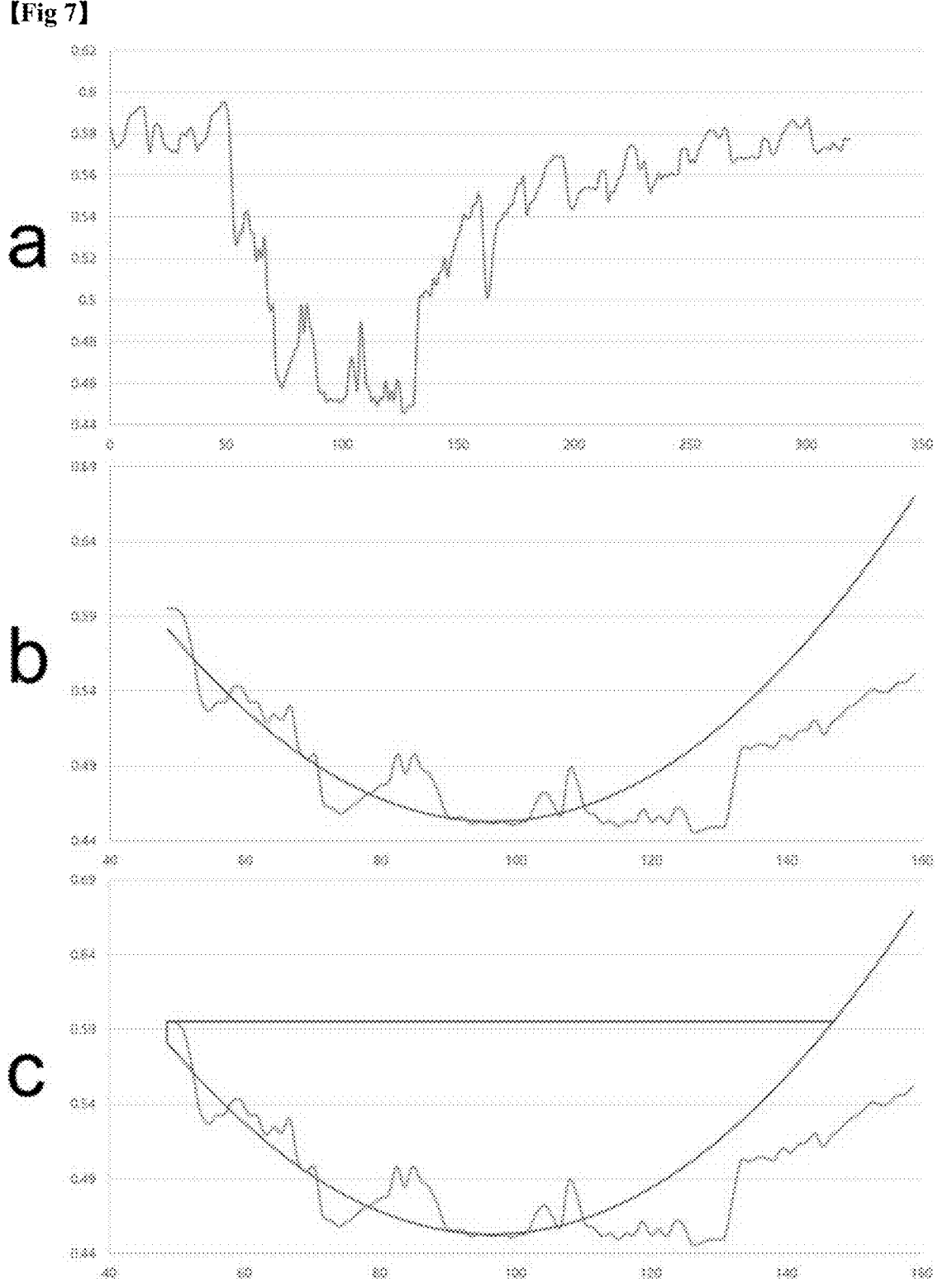

METHOD FOR PROVIDING INFORMATION NECESSARY FOR EVALUATING SEVERITY OF CORONARY ARTERY STENOSIS

CROSS-REFERENCE TO RELATED APPLICATION(S)

Pursuant to 35 U.S.C. § 119(e), this application is a continuation of International Application No. PCT/KR2022/003894, with an international filing date of Mar. 21, 2022, which claims the benefit of priority to Korean Patent Application No. 10-2021-0036100, filed on Mar. 19, 2021, in the Korean Intellectual Property Office, the contents of which are hereby incorporated by reference herein in their entirety.

BACKGROUND

Field of the Description

The present disclosure relates to a method for providing information necessary for assessing the severity in the coronary artery stenosis.

Related Art

Coronary arteries, located on the outer surface of the heart, are divided into left and right coronary arteries and supply oxygen to the heart. When blood flow is obstructed within the coronary arteries due to stenosis or other factors, it can lead to diseases such as angina pectoris.

In patients suspected of coronary artery disease, the most fundamental examination is angiography. Angiography is a technique that involves inserting a catheter into the body to reach the target area's blood vessels and administering contrast agents. When radiographing the area of blood vessels where a contrast agent is administered, the blood vessels where the contrast agent is located appear dark, allowing for the visualization of the vascular anatomical structure. Stenosis greater than 70% is generally considered to require an intervention procedure, while stenosis between 50% and 70% requires the evaluation to determine the need for the intervention procedure.

Methods for assessing the physiological severity of stenosis within the coronary arteries include Fractional Flow Reserve (FFR) and instantaneous Wave-free Ratio (iFR). FFR is a technique used to measure the pressure in the area where stenosis is suspected. First, a hyperemic agent is administered, and then a catheter with a pressure sensor is inserted into the region of interest in the coronary arteries to measure proximal and distal pressures. The pressure ratio is then calculated by dividing the distal pressure by the proximal pressure, and if the pressure ratio is 0.8 or less, it is considered to be physiologically serious stenosis. However, FFR can lead to additional costs, vascular damage by the catheter, discomfort from the hyperemic agent causing chest pain and heart rate reduction.

iFR is similar to FFR in that it sets the proximal and distal areas of the region of interest and measures the pressures. However, it differs by measuring pressure over a specific time through the setting a cycle and calculating the pressure ratio using pressure data when the coronary arteries are at rest. Unlike FFR, iFR does not require the hyperemic agent but can still cause vascular damage due to the catheter.

SUMMARY

A technical object of the disclosure is to provide a method that can safely and easily provide information necessary for assessing severity of the coronary artery stenosis.

Additionally, it provides a technology for tracking coronary arteries that continuously change position during taking an angiography.

According to an exemplary embodiment of the present disclosure, a method for providing information necessary for assessing severity of coronary artery stenosis includes: administering a contrast agent to a coronary artery; capturing an angiographic image; setting a suspected stenosis area where stenosis is suspected and a proximal area where blood passes before the suspected stenosis area within region of captured image for observing the coronary artery stenosis based on the captured angiographic image; fixing position of the coronary artery where the contrast agent is administered by image processing; and deriving a blood flow velocity ratio, which is a relative ratio of blood flow in the proximal area and the suspected stenosis area, based on time when brightness changes in the proximal area and the suspected stenosis area of the captured image.

According to an exemplary embodiment of the present disclosure, a method for providing information necessary for assessing severity of coronary artery stenosis includes: capturing an angiographic image for a contrast agent administered into a coronary artery; fixing position of the coronary artery where the contrast agent is administered by image processing; and deriving a blood flow velocity ratio in first area and second area within region of captured image for observing the coronary artery stenosis, the first area is set as suspected stenosis area and the second area is set as proximal area where blood passed before, based on the captured angiographic image, wherein the deriving the blood flow velocity ratio is derived as a relative ratio of blood flow in the first area to blood flow in the second area, based on time when brightness captured in the first area and the second area changes.

The position of the coronary artery where the contrast agent is administered may be determined by setting a threshold, binarizing the angiographic image in grayscale to distinctly define boundaries of the coronary artery, setting a cycle for the coronary artery, tracking the boundaries of the coronary artery that change position during the cycle for the coronary artery and correcting the captured image into a still image.

One cycle for the coronary artery may be determined by matching times of peaks occurred in an electrocardiogram with the captured angiographic image after simultaneously measuring an electrocardiogram while capturing the angiographic image.

The blood flow velocity ratio may be derived by dividing the blood flow in the suspected stenotic area by the blood flow in the proximal area.

The blood flow in the suspected stenotic area may be derived by measuring the brightness of the suspected stenotic area over time, calculating integral value of the brightness and dividing an initial amount of the contrast agent administered by the integral value.

The blood flow in the proximal area may be derived by measuring the brightness of the proximal area over time, calculating integral value of the brightness and dividing an initial amount of the contrast agent administered by the integral value.

Furthermore, according to an exemplary embodiment of the present disclosure, a method for providing information necessary for assessing severity of coronary artery stenosis comprising: administering a hyperemic agent to dilate blood vessel in region of interest; administering a contrast agent to a coronary artery; capturing an angiographic image; setting the region of interest and a proximal area where blood passes before the region of interest within region of the captured image based on the captured angiographic image; fixing position of the coronary artery where the contrast agent is administered by image processing; and deriving a contrast agent flow ratio corresponding to a ratio of time when brightness changes in the proximal area of the captured image to time when brightness changes in the proximal area administering the contrast agent without the hyperemic agent.

Furthermore, according to an exemplary embodiment of the present disclosure, a method for providing information necessary for assessing severity of coronary artery stenosis comprising: capturing an angiographic image for a contrast agent administered into a coronary artery which is dilated by a hyperemic agent; fixing position of the coronary artery where the contrast agent is administered by image processing; and deriving a contrast agent flow ratio in first area and second area within region of the captured image, the first area is set as region of interest and the second area is set as proximal area where blood passed before, based on the captured angiographic image, wherein the deriving the contrast agent flow ratio is derived in correspondence with a ratio of time when brightness captured in the first area and the second area changes to time when brightness changes occur in the first area and the second area of the coronary artery administering the contrast agent without the hyperemic agent.

Furthermore, according to an exemplary embodiment of the present disclosure, the device includes a contrast agent administering unit, a capturing unit, an image setup unit, an image processing unit and a stenosis detecting unit; the contrast agent administering unit administers the contrast agent to the coronary artery; the capturing unit captures the angiographic image: the image setup unit sets the suspected stenosis area where stenosis is suspected and the proximal area where blood passes before the suspected stenosis area based on the angiographic image captured within the region of the captured image and the QCA result; the image processing unit fixes the position of the coronary artery where the contrast agent is administered by processing of the captured images; the stenosis detecting unit derives the blood flow velocity ratio, which is the relative ratio of the blood flow between the proximal area and the suspected stenosis area, based on the time when the brightness changes in the proximal area and the suspected stenosis area of the captured image.

According to the exemplary embodiment of the present disclosure, by binarizing the angiographic image so that only black or white is displayed, the boundaries of the coronary arteries into which the contrast agent is administered is clearly defined, making it easier to visually track the blood vessels.

According to the exemplary embodiment of the present disclosure, by image processing to fix the position of the coronary arteries in the angiographic image, the blood flow of the blood vessels within the region of interest can be easily measured.

According to the exemplary embodiment of the present disclosure, information necessary for detecting stenosis of the coronary arteries can be provided by measuring the time it takes for the contrast agent to pass through the coronary arteries, calculating the velocity ratio between the proximal area and the suspected stenosis area.

BRIEF DESCRIPTION OF DRAWINGS

FIG. 1 is a radiographic image of coronary arteries with contrast agent administration (QCA: quantitative coronary angiography).

FIG. 2A is a captured photograph of an angiographic image, and FIG. 2B is a photograph after binary processing of FIG. 2A.

FIG. 3A is an electrocardiogram graph, FIG. 3B is a graph illustrating a change in position of a proximal area over time, and FIG. 3C is a graph illustrating a change in position of a suspected stenosis area over time.

FIGS. 4A to 4C illustrate a change in an angiographic image over time.

FIGS. 5A to 5C illustrate a change in a corrected angiographic image over time.

FIG. 6A is a graph illustrating a change in brightness over time in the proximal area, FIG. 6B is an enlarged graph of FIG. 6A, and FIG. 6C is a graph illustrating a region of integration of FIG. 6B.

FIG. 7A is a graph illustrating a change in brightness over time in the suspected stenosis area, FIG. 7B is an enlarged graph of FIG. 7A, and FIG. 7C is a graph illustrating a region of integration of FIG. 7B.

DETAILED DESCRIPTION

Hereinafter, embodiments of the present disclosure will be described in detail with reference to the accompanying drawings, so that those skilled in the art having ordinary knowledge in the technical field to which the present disclosure belongs can easily carry out the present disclosure. However, it should be understood that the present disclosure can be implemented in various ways and is not limited to the embodiments described here. Throughout the specification, the same reference numerals are assigned to identical or similar parts.

Since the present disclosure can have various modifications and embodiments, specific examples are illustrated in the drawings and described in detail to facilitate understanding. However, this is not intended to limit the present disclosure to specific embodiments, and it should be understood that the present disclosure encompasses all modifications, equivalents, or alternatives within the spirit and scope of the invention.

In describing the present disclosure, detailed explanations of related prior art may be omitted if it is deemed to unnecessarily obscure the essence of the present disclosure. Furthermore, numerical labels (e.g., "first," "second," etc.) used in the description of this specification are merely identification symbols to distinguish one component from another.

Furthermore, throughout the specification, when one component is described as being "connected" to another component, it should be understood that the one component may be directly connected to the other component or may be connected through another component unless there is explicit description to the contrary. Also, when a part is described as "including" another part, this does not exclude other parts, but means that it may include other parts unless there is explicit description to the contrary. Additionally, in this specification, terms such as "device," "system," "unit," "module," and the like refer to units that process at least one function or operation and may be implemented by one or more hardware (processors) or software (programs), or a combination of hardware and software.

Now, the method for detecting stenosis of the coronary arteries according to an exemplary embodiment of the present disclosure will be described with reference to FIGS. 1 to 7C.

FIG. 1 is a radiographic image of coronary arteries with contrast agent administration (QCA: quantitative coronary angiography), FIG. 2A is a captured photograph of an angiographic image, FIG. 2B is a photograph after binary processing of FIG. 2A, FIG. 3A is an electrocardiogram graph, FIG. 3B is a graph illustrating a change in position of a proximal area over time, FIG. 3C is a graph illustrating a change in position of a suspected stenosis area over time, FIGS. 4A to 4C illustrate a change in an angiographic image over time, FIGS. 5A to 5C illustrate a change in a corrected angiographic image over time, FIG. 6A is a graph illustrating a change in brightness over time in the proximal area, FIG. 6B is an enlarged graph of FIG. 6A, FIG. 6C is a graph illustrating a region of integration of FIG. 6B, FIG. 7A is a graph illustrating a change in brightness over time in the suspected stenosis area, FIG. 7B is an enlarged graph of FIG. 7A, and FIG. 7C is a graph illustrating a region of integration of FIG. 7B.

<Contrast Agent Administration and Imaging>

When blood vessels are imaged, the boundaries of the blood vessels are unclear and difficult to track. Therefore, imaging is only possible by administering a contrast agent that does not allow the passage of radiation. For this reason, a contrast agent is administered to coronary arteries to capture radiographic images. Substances that may be used as contrast agents include iodine, barium, and gadolinium. Iodine and gadolinium may be used as the contrast agent in radiographic images, and gadolinium may be used as the contrast agent in magnetic resonance imaging (MRI) images.

To administer the contrast agent to the coronary arteries located in the heart, a thin catheter smaller than the blood vessels is inserted into the body. The catheter capable of administering the contrast agent passes through the arteries and positions itself in the heart to administer the contrast agent. Typically, the catheter is inserted through femoral arteries, but it may also be inserted through other parts of the human body.

After the administration of the contrast agent, angiographic images are taken. Imaging techniques may be performed using radiation, computed tomography (CT), or magnetic resonance imaging (MRI). Referring to FIG. 1, the areas of the blood vessels through which the contrast agent passes appear dark, while other areas appear bright in the captured image. The captured image is stored and may be used to provide information necessary for the subsequent assessment of stenosis severity. Furthermore, through the captured image, the approximate shape of the coronary arteries may be determined, allowing for the estimation of areas where stenosis may occur.

<Setting Region of Interest>

In the present disclosure, the region of interest 110 refers to the region to be observed in the coronary artery. The area where blood passes before the area suspected of stenosis is defined as the proximal area 111, and the area where stenosis is suspected is defined as the suspected stenosis area 112. In this regard, reference can be made to quantitative coronary angiography (QCA), which is commonly employed in angiographic imaging. QCA is a technique widely used in the medical field for assessing coronary artery stenosis in coronary angiography, such as in stent procedures or vascular treatments. In other words, QCA results may be used to distinguish the regions of interest, stenosis estimated areas, proximal area, etc.

<Binary Image Processing>

Referring to FIGS. 2A and 2B, FIG. 2A is the angiographic image in the grayscale, FIG. 2B is the image that has been binarized in black and white to clearly define the boundaries of the blood vessels. Binary image processing involves setting a specific brightness threshold. If the brightness is above the threshold, it is changed to white, and if it is below, it is changed to black. In the binarized image, the parts where the contrast agent passes through the blood vessels appears black, while the boundaries of the blood vessels appear white. This may make it easier to track the region of interest. During the binary image processing, the threshold value may be set using the Adaptive Thresholding method in the calibration software, but it is not limited to using the Adaptive Thresholding method. Otsu's method is used to set the Adaptive Thresholding method. Otsu's method is a technique where the threshold that minimizes the variance for each region of the image is set.

<Setting Coronary Artery Cycle>

To determine the rates of the contrast agent inflow and outflow in the coronary artery, it needs to understand one cycle for the coronary artery. Since it is difficult to determine one cycle based on the image alone, simultaneous electrocardiogram (ECG) measurements are taken when capturing the angiographic image after administering the contrast agent.

Referring to FIGS. 3A to 3C, since ECG data of the electrocardiogram represents the cardiac beat cycle, matching the times of peaks observed in the ECG data with the angiographic image allows for confirmation of one cycle related to the coronary artery.

FIG. 3A is the graph illustrating the changes in the electrocardiogram over time, FIG. 3B is the graph illustrating the changes in the position of the proximal area over time, and FIG. 3C is the graph illustrating the changes in the position of the suspected stenosis area over time. In FIG. 3A, the sampling rate is 400 frames per second, while in 3B and 3C, the sampling rate is 30 frames per second. Therefore, 1 frame in FIG. 3A corresponds to 0.0025 seconds, and in 3B and 3C, 1 frame corresponds to 0.033 seconds.

In FIG. 3A, R represents the number of frames where the peaks of the ECG occur. The interval between ECG peaks corresponds to one cycle of cardiac beats, which is equivalent to one cycle for the coronary artery. Therefore, by converting the frame count of the R value in FIG. 3A into time and then into frames per second (30 frames per second), it is possible to find the start and end of one cycle for the coronary artery in 3B and 3C. However, ECG signal contains irregular data within one cycle for the coronary artery. Therefore, linear interpolation may be used to correct the ECG data and facilitate tracking the position of the coronary artery.

With the binarized image where the boundaries of the blood vessels are clearly defined and the number of frames (time) when the blood vessel's cycle occurs, it becomes possible to track the region of interest as the contrast agent passes through the coronary artery during one cycle for the coronary artery.

<Still Image Processing for Moving Coronary Arteries>

Referring to FIGS. 4A to 4C, the region of the coronary artery to be observed in the angiographic image is represented by the inner rectangle, and this region continuously changes its position. Therefore, the observer needs to continuously shift their gaze to track the coronary artery, making it difficult to grasp the shape of the coronary artery.

Based on the tracked positions of the coronary artery, the angiographic image showing the continuous movement of the coronary artery may be corrected into the still image. Referring to FIGS. 5A to 5C, an arbitrary point is pre-set as the location where the coronary artery becomes fixed, and when the image itself moves, the still image of the coronary artery is generated. The inner rectangle represents the region of the coronary artery to be observed, and after image processing, this region becomes fixed at a single point. The observer may now grasp the shape of the coronary artery without continuously shifting their focus. Additionally, observing changes in brightness occurring in the coronary artery becomes more convenient.

<Brightness Quantification>

In the angiographic image, the blood vessels become dark as the contrast agent passes through the coronary arteries, and when the contrast agent passes, the blood vessels become bright again. Therefore, the changes in brightness over time may be quantified, as shown in FIGS. 6A to 7C. The horizontal axes in FIGS. 6A to 7C represent the number of frames, where 1 frame means 0.033 seconds.

Referring to FIGS. 6A and 7A, because the low points in the graphs correspond to the darkest parts, it may be seen that the low points indicate the passage of the contrast agent and the high points after the low points represent the influx of blood after the contrast agent has passed. Therefore, based on the time of the brightness changes, the time when the contrast agent to pass through the coronary artery may also be determined.

The change in brightness corresponds to changes in the concentration of the contrast agent, and by calculating the Stewart-Hamilton Equation based on concentration changes, blood flow may be calculated.

<Calculation of Blood Flow Velocity Ratio>

Using the Equations 1 and 2 below, it is possible to calculate the blood flow velocity ratio between the proximal area and the suspected stenosis area. A higher blood flow velocity ratio indicates a higher possibility of stenosis, so it may provide information necessary for detecting coronary artery stenosis.

$$Q = \frac{I}{\int Cidt}$$ [Equation 1]

Q=Blood Flow
I=Volume of Administered Contrast Agent
$\int_{Ctdt}$=Integral of the Contrast Agent Concentration Change Over Time The above equation is the Stewart-Hamilton Equation used to calculate the blood flow passing through the region of interest in the coronary artery, which includes the proximal area and the suspected stenosis area. The time range for the concentration change of the contrast agent over time is emphasized in between frames 50 and 150 on the x-axis within the graphs in FIGS. 6A and 7A, and by integrating this portion, the integral of the contrast agent concentration change over time may be determined.

FIG. 6B is the enlarged and extrapolated graph of the emphasized portion of FIG. 6A, and FIG. 7B is the enlarged and extrapolated graph of the emphasized portion of FIG. 7A. Extrapolated graphs facilitate integration, and by calculating the area of the closed half-arc shape region shown in FIGS. 6C and 7C, the integral value of the contrast agent concentration change over time may be determined.

By dividing the volume of the administered contrast agent by the integral value of the contrast agent concentration change over time, the blood flow in the proximal area and the stenosis suspected area within the region of interest may be calculated.

$$VR = \frac{Q_s}{Q_s^N}$$ [Equation 2]

VR=Blood Flow Velocity Ratio
$Q_s$=Blood Flow in the Stenosis Suspected Area
$Q_s^N$=Blood Flow in the Proximal Area The above equation is used to determine the blood flow velocity ratio between the proximal area and the suspected stenosis area within the coronary artery. Based on the blood flow in the proximal area and the suspected stenosis area obtained through Equation 1, the blood flow velocity ratio may be calculated by dividing the blood flow in the stenosis suspected area by the blood flow in the proximal area. The blood flow velocity ratio calculated based on the data from FIGS. 6A to 7C is 1.2385.

<Calculation of Contrast Agent Velocity in Stenosis Suspected Area Depending on Hyperemic Agent Administration>

According to an exemplary embodiment of the present disclosure, in addition to calculating the velocity ratio between the proximal area and the stenosis suspected area, it is also possible to estimate Coronary Flow Reserve (CFR). By comparing the contrast agent flow in the stenosis suspected area when the hyperemic agent is administered and when they are not, information necessary for detecting coronary artery stenosis may be provided.

The hyperemic agent acts on the vascular wall, causing vascular muscles to move and expanding blood vessels. Adenosine may be used as the hyperemic agent, but the hyperemic agent is not limited to adenosine. After administering the hyperemic agent and the contrast agent and capturing images, by determining the cycle for the coronary artery and image processing, changes in brightness over time may be observed as the contrast agent passes through the stenosis suspected area. By calculating the integral value of brightness changes and dividing the amount of the contrast agent administered by the integral value, the blood flow in the hyperemic state may be determined. Based on the blood flow in the hyperemic state and the baseline state, CFR may be calculated using Equation 3.

$$CFR = \frac{Q_h}{Q_b}$$ [Equation 3]

CFR=Coronary Flow Reserve
$Q_h$=Blood Flow in Hyperemic State
$Q_b$=Blood Flow in Baseline State The above mathematical equation is used to determine the CFR. The blood flow in the hyperemic state and the blood flow in the baseline state may be obtained through Equation 1. By dividing the blood flow in the hyperemic state by the blood flow in the baseline state, the CFR may be determined.

Furthermore, the method for providing information necessary for detecting coronary artery stenosis, as described above, may be implemented by a device (system) for assessing the severity in coronary artery stenosis. The device may include a contrast agent administering unit, a capturing unit, an image setup unit, an image processing unit and a stenosis detecting unit. The contrast agent administering unit may administer the contrast agent to the coronary artery. The capturing unit may capture the angiographic image. The image setup unit may set the suspected stenosis area where stenosis is suspected and the proximal area where blood passes before the suspected stenosis area based on the angiographic image captured within the region of the captured image and the QCA result. The image processing unit may fix the position of the coronary artery where the contrast agent is administered by processing of the captured images. The stenosis detecting unit may derive the blood flow velocity ratio, which is the relative ratio of the blood flow between the proximal area and the suspected stenosis area, based on the time when the brightness changes in the proximal area and the suspected stenosis area of the captured image.

While preferred embodiments of the present disclosure have been described in detail above, it is understood that the scope of the present disclosure is not limited thereto, and various modifications and improvements made by those skilled in the art utilizing the basic concepts of the present disclosure defined in the following claims also fall within the scope of the present disclosure.

The present disclosure is capable of various modifications and can have various embodiments, and specific embodiments have been illustrated and described in detail in the drawings and the detailed description. However, it should be understood that this is not intended to limit the present disclosure to the particular forms set forth, but to cover all modifications, equivalents, and alternatives falling within the scope and spirit of the inventive concept and the technological teachings of the present disclosure.

Throughout the specification, when a certain portion is referred to as "including" a certain component, it means that the portion may further include other components rather than excluding other components, unless specifically stated to the contrary. Additionally, terms such as "device," "system," "unit," "module," and the like used throughout the specification refer to units capable of performing at least one function or operation. These units include one or more hardware (processors), software (programs), or a combination of hardware and software to implement the method for providing information necessary for assessment of stenosis severity in the coronary arteries as described herein.

What is claimed is:

1. A method for providing information necessary for assessing severity of coronary artery stenosis comprising:
 administering a contrast agent to a coronary artery;
 capturing an angiographic image;
 setting a suspected stenosis area where stenosis is suspected and a proximal area where blood passes before the suspected stenosis area within region of captured image for observing the coronary artery stenosis based on the captured angiographic image;
 fixing position of the coronary artery where the contrast agent is administered by image processing; and
 deriving a blood flow velocity ratio, which is a relative ratio of blood flow in the proximal area and the suspected stenosis area, based on time when brightness changes in the proximal area and the suspected stenosis area of the captured image,
 wherein the position of the coronary artery where the contrast agent is administered is determined by setting a threshold, binarizing the angiographic image in grayscale to distinctly define boundaries of the coronary artery, setting a cycle for the coronary artery, tracking the boundaries of the coronary artery that change position during the cycle for the coronary artery and correcting the captured image into a still image,
 wherein one cycle for the coronary artery is determined by matching times of peaks occurred in an electrocardiogram with the captured angiographic image after simultaneously measuring an electrocardiogram while capturing the angiographic image,
 wherein the blood flow velocity ratio is derived by dividing the blood flow in the suspected stenotic area by the blood flow in the proximal area,
 wherein the blood flow in the suspected stenotic area is derived by measuring the brightness of the suspected stenotic area over time, calculating integral value of the brightness and dividing an initial amount of the contrast agent administered by the integral value, and
 wherein the blood flow in the proximal area is derived by measuring the brightness of the proximal area over time, calculating integral value of the brightness and dividing an initial amount of the contrast agent administered by the integral value.

2. A method for providing information necessary for assessing severity of coronary artery stenosis comprising:
 administering a contrast agent to a coronary artery of a patient without a hyperemic agent and capturing a first angiographic image sequence while simultaneously measuring an electrocardiogram (ECG);
 administering a hyperemic agent to dilate a coronary artery in a region of interest, administering the contrast agent, and capturing a second angiographic image sequence while simultaneously measuring the ECG;
 in each of the first and second sequences, setting a region of interest corresponding to a suspected stenosis area based on the captured angiographic image;
 in each of the first and second sequences, automatically fixing, by image processing, a position of the coronary artery by: setting a brightness threshold; binarizing grayscale angiographic frames to distinctly define coronary-artery boundaries; determining a coronary-artery cycle by matching times of ECG peaks to the captured frames; tracking boundary positions that change during the cycle; and motion-compensating the sequence into a still image;
 in each of the first and second sequences, measuring brightness in the region of interest over time, computing an integral of a brightness-change curve over time, and calculating a blood-flow value for the region of interest by dividing an initial amount of the administered contrast agent by the corresponding integral; and
 deriving a coronary flow reserve as a contrast-agent flow ratio by dividing the blood-flow value calculated from the second sequence by the blood-flow value calculated from the first sequence.

* * * * *